United States Patent [19]

Yamato

[11] Patent Number: 5,128,345
[45] Date of Patent: Jul. 7, 1992

[54] CARCINOSTATIC COMPOSITION COMPRISING INDOLQUINOLINES

[75] Inventor: Masatoshi Yamato, Okayama, Japan

[73] Assignee: Mect Corporation, Tokyo, Japan

[21] Appl. No.: 318,256

[22] Filed: Mar. 3, 1989

[30] Foreign Application Priority Data

Mar. 10, 1988 [JP] Japan .................. 63-56883

[51] Int. Cl.$^5$ ............... C07D 471/04; C07D 221/18; A61K 31/435
[52] U.S. Cl. ........................ 514/285; 546/70
[58] Field of Search .......................... 546/70; 514/285

[56] References Cited

U.S. PATENT DOCUMENTS 4,826,850 5/1989 Yamato ..................... 546/62

OTHER PUBLICATIONS

Merck Manual, [Rahway, N.J. Merck and Co. 1987], pp. 2306 to 2309.
Yamato et al., J. Med. Chem., vol. 32, No. 6, pp. 1295-3000 (1989).
Atwell et al., J. Med. Chem., vol. 15 (6), pp. 611-615 (1972).
Cain et al., J. Med. Chem., vol. 17 (9), pp. 422-430 (1974).
Cain et al., J. Med. Chem., vol. 18 (11), pp. 3881-3884 (1979).
Van Echo et al., Canc. Res. 39, pp. 3881-3884 (Oct. 1979).
Dziewonski et al., Chem. Abs., vol. 59 (10), entry 11365d (1963).

*Primary Examiner*—Robert T. Bond
*Assistant Examiner*—Edward C. Ward
*Attorney, Agent, or Firm*—Oblon, Spivak, McClelland, Maier & Neustadt

[57] ABSTRACT

Novel indoloquinoline compounds of formula (I), benzo(b)acridines of formula (II) and benzo(c)acridines of formula (III) have carcinostatic activities. The compounds, processes for preparing the compounds via nucleophilic aromatic substitution, and carcinostatic compositions containing the same are disclosed.

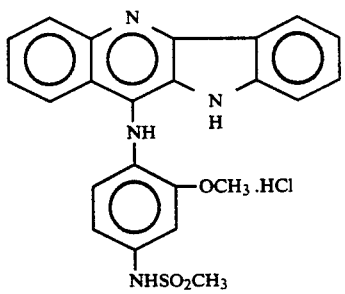

(1)

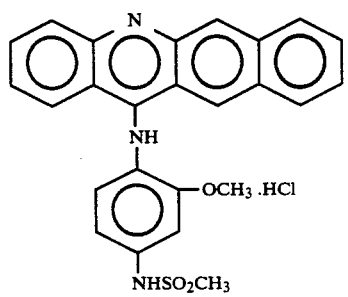

(2)

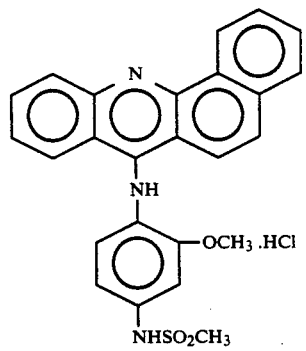

(3)

2 Claims, No Drawings

CARCINOSTATIC COMPOSITION COMPRISING INDOLQUINOLINES

BACKGROUND OF THE INVENTION

1. Field of the Invention

The present invention relates to novel quinoline system compounds (more particularly, indoloquinoline system compounds) and novel acridine system compounds (more particularly, benzo(b)acridine system compounds and benzo(c)acridine system compounds) which have carcinostatic activities. The present invention further relates to processes for preparing the aforementioned compounds and carcinostatic compositions containing the same.

2. Prior Art Statement

B. F. Cain, G. J. Atwell and R. N. Sealye synthesized various acridine system compounds each having an alkylamino group at the 9-position, and found that they have antileukemia activities (see J. Med. Chem., vol 15, 611 (1972)).

Cain, Atwell and Sealy further replaced the alkylamino group at the 9-position of acridine with another molecule or group and found that N-(4-(9-acridylamino)-3-methoxyphenyl)methanesulfonamide (Amsacrine) has the highest carcinostatiac function. (Refer to J. Med. Chem., vol. 17, 922 (1974).) On the other hand, G. W. Rewcastle, B. C. Baguley, G. J. Atwell and W. A. Denny modified the Amsacrine molecule to synthesize derivatives each having an acridine ring introduced with a methyl group or N-methylcarbamoyl group, and found that the derivatives have strong carcinostatic activities. (Refer to J. Med. Chem., vol. 30, 1576 (1987).)

We previously synthesized indenoquinoline system compounds having high carcinostatic activities, and filed Patent Application relating to them. (See Japanese Patent Appln. No. 246776/1986.)

We further synthesized novel benzofuroquinoline and benzothienoquinoline system compounds having similar high carcinostatic activities, and filed another Patent Application relating to them. (See Japanese Patent Appln. No. 69766/1987.)

OBJECTS AND SUMMARY OF THE INVENTION

The present invention is based on our further investigations, and relates to indoloquinoline and benzoacridine system compounds, processes for preparing the same and uses thereof as carcinostatic agents.

According to a first aspect of this invention, there is provided an indoloquinoline system compound represented by the following formula (1):

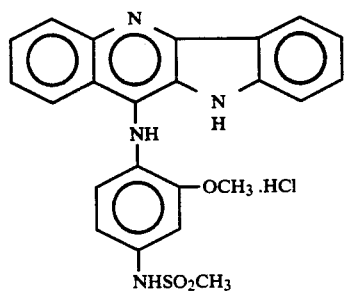

(1)

Further provided by the invention is a process for preparing a condensed quinoline system compound represented by the following formula (1):

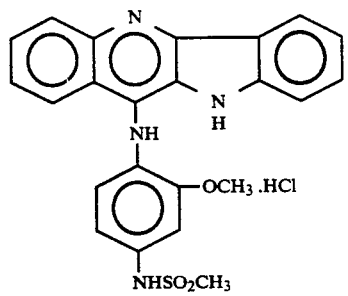

(1)

characterized in that a compound represented by the following formula (4):

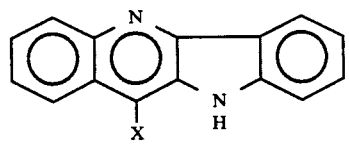

(4)

wherein X stands for a halogen atom; is allowed to react with a compound represented by the following formula (5):

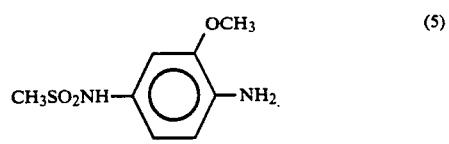

(5)

According to a second aspect of this invention, there is provided a benzo(b)acridine system compound represented by the following formula (2):

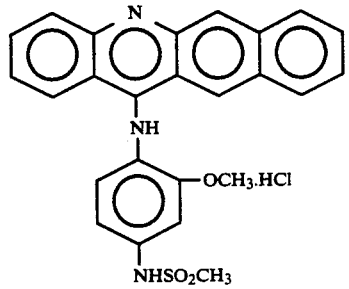

(2)

Another object of this further provided by the invention is to provide a process for preparing a condensed acridine system compound represented by the following formula (2):

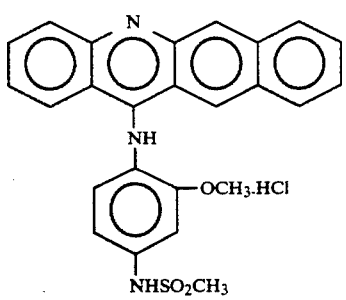

(2)

characterized in that a compound represented by the following formula (6):

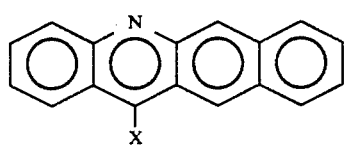

(6)

wherein X stands for a halogen atom; is allowed to react with a compound represented by the following formula (5):

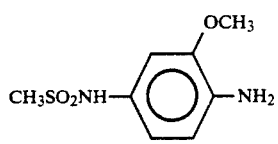

(5)

According to a third aspect of this invention, there is provided a benzo(c)acridine system compound represented by the following formula (3):

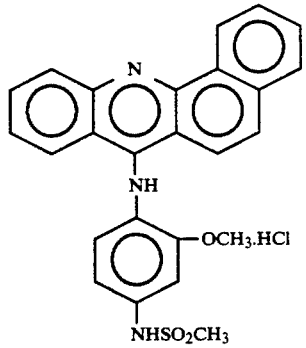

(3)

Further provided by the invention is a process for preparing a benzo(c) acridine system compound represented by the following formula (3):

characterized in that a compound represented by the following formula (7):

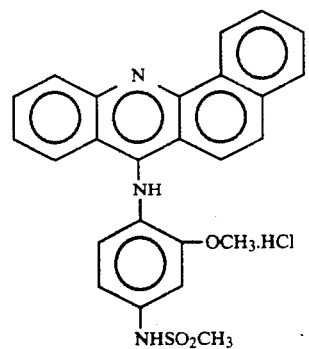

(3)

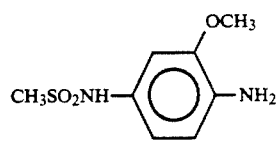

(7)

wherein X stands for a halogen atom; is allowed to react with a compound represented by the following formula (5):

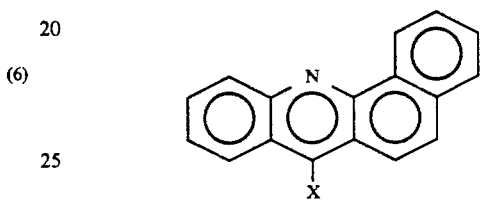

(5)

According to a further aspect of this invention, there is provided a carcinostatic composition containing, as an efficacious ingredient, at least one of the compounds represented by any one of the following formulae (1), (2) and (3):

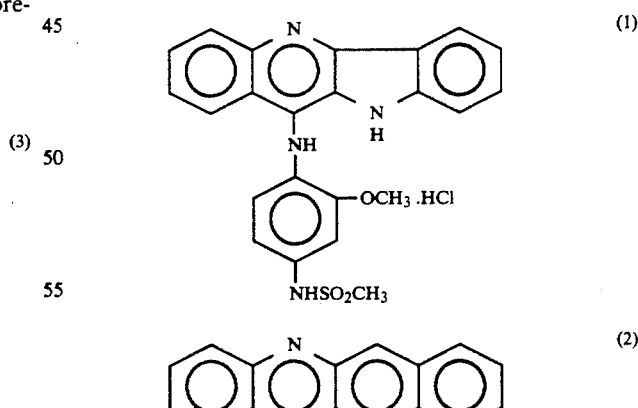

(1)

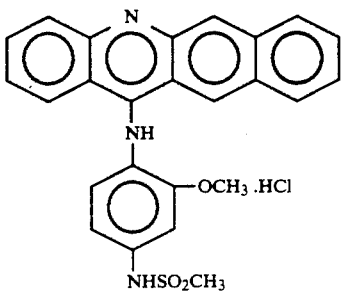

(2)

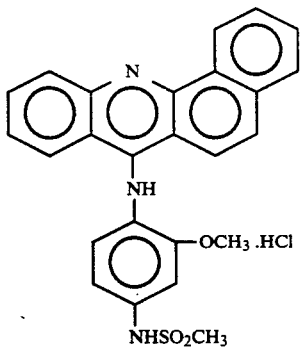

EXAMPLES OF THE INVENTION

The present invention will be described in detail by referring to some preferred embodiments. However, it should be noted that the invention is not limited to the following specific examples and may be modified or altered within the scope of the invention clearly defined by the appended claims.

EXAMPLE 1

Preparation of N-)4-((indolo(3,2-b)quinoline-10-yl)-amino)-3-methoxyphenyl)methanesulfonamide Compound (1)

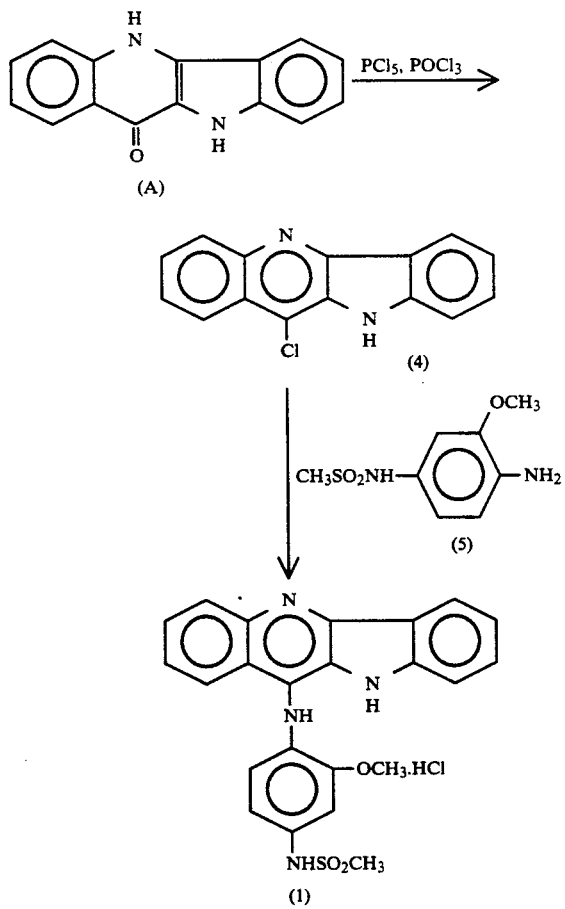

The step of preparing the Compound (4) from the starting material (A) has been reported by Klaus Gorlitzer and Josef Weber in Arch. Pharm. vol. 341, 852 (1981).

505 mg of the Compound (4) prepared by the method of Gorlitzer and Weber was dissolved in 8 ml of ethoxyethanol, pyridine dioxane or dimethylformamide together with 432 mg of the Compound (5), and heated to reflux for 6 hours while being added with a few drops of conc. hydrochloric acid if necessary. The separated crystal was filtered and recrystallized from ethanol to obtain 600 mg of the compound (1). The yield was 72%.

Melting Point: 280° to 282° C. (Decomposition Point)
NMR(DMSO-$d_6$)
$\delta$3.08 (3H, s, SO$_2$CH$_3$),
3.52 (3H, s, OCH$_3$);
6.70 to 7.16 (3H, m, Ar-H),
7.32 to 7.82 (7H, m, Ar-H and NH x 2);
8.12 to 8.64 (3H, m, Ar-H);
11.03 to 11.20 (1H, b, NH).

EXAMPLE 2

Preparation of N-(4-((benzo(b)acridine-12yl)amino)-3-methoxyphenyl)methanesulfonamide Compound 2

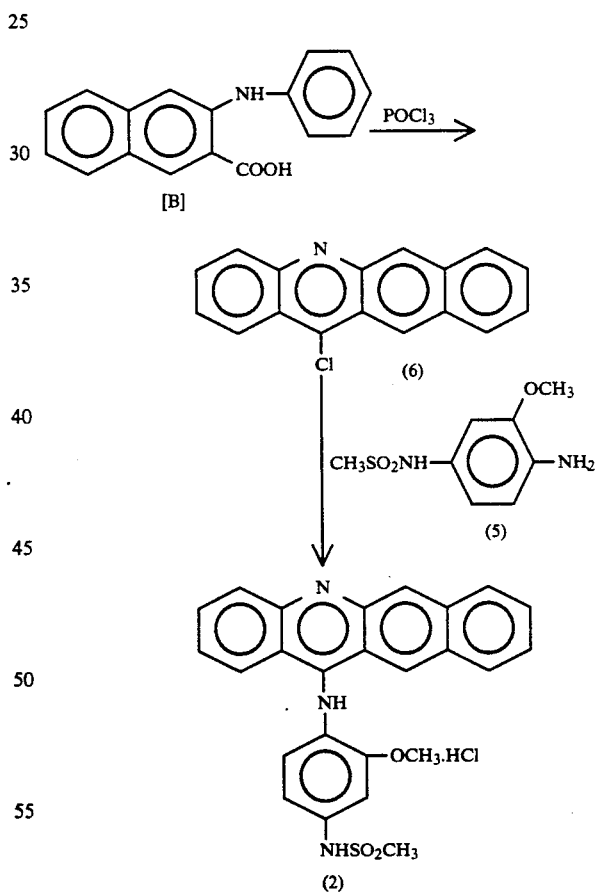

The step for preparing the Compound (6) from the starting material (B) is the same as reported by A. Albert, D. J. Brown and H. Duewell in J. Am. Chem. Soc., vol. 70, 1284 (1948). 825 mg of the Compound (6) and 678 mg of the Compound (5) were dissolved in 10 ml of ethoxyethanolpyridinedioxane or dimethylformamide, and heated to reflux for an hour while being added with a few drops of conc. hydrochloric acid if necessary. The separated precipitate was filtered and recrystallized from dimethylformamide to obtain 800 mg of the Compound (2). The yield was 61%.

Melting Point: above 300° C. (Decomposition Point).
NMR (DMSO-$d_6$)
δ2.92 (3H, s, $SO_2CH_3$),
3.48 (3H, s, $OCH_3$),
6.82 to 7.20 (3H, m, Ar-H),
7.42 to 8.12 (9H, m, Ar-H and NH),
8.31 to 8.39 (1H, m, Ar-H),
9.13 to 9.20 (1H, m, Ar-H);
10.10 to 10.17 (1H, b, NH).

EXAMPLE 3

Preparation of N-(4-(benzo(c) acridine-11-yl) amino)-3-methoxyphenyl)methanesulfonamide Compound (3)

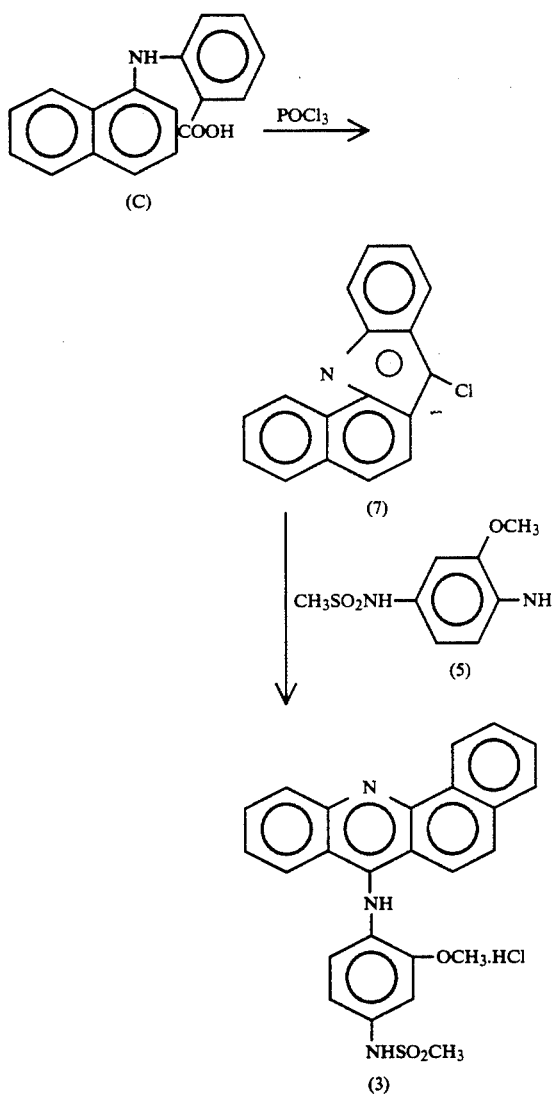

The compound (7) was prepared from the starting material (C) through the step as reported by G. B. Bachman and G. M. Picha in J. Am. Chem. Soc., vol. 68, 1599 (1946).

825 mg of the thus prepared Compound (7) and 678 mg of the Compound (5) were dissolved in 8 ml of methoxyethanol, pyridinedioxane or dimethylformamide, being added with a few drops of conc. hydrochloric acid if necessary, and heated to reflux for 3 hours. The separated crystal was filtered and recrystallized from dimethylformamide to obtain 850 mg of the Compound (3). The yield was 61%.

Melting Point: above 300° C. (Decomposition Point)
NMR (DMSO-$d_6$)
δ: 3.10 (3H, s, $SO_2CH_3$),
3.41 (3H, s, $OCH_3$),
7 15 to 7.32 (3H, m, Ar-H);
7.48 to 8.17 (9H, m, Ar-H and NH),
8.33 to 8.46 (1H, m, Ar-H),
8.93 to 9.23 (1H, m, Ar-H),
9.82 to 9.94 (1H, b, NH).

Ingredient Example 1 (Injection)

500 mg of each of the Compounds (1), (2) and (3) was separately dissolved in 19.6 ml of a 0.85% physical saline solution to prepare an intravenous injection. Each injection was administered intravenously at a dose of 20 ml a day.

TEST EXAMPLE 1

Test for Antitumorigenic Function

1) Function for Inhibiting Multiplication of KB-1 Cell (in vitro test)

KB cells, carcinomatous cell tumors, were transferred to in vitro floatation incubator systems, and added respectively with the Compounds (1), (2) and (3). The results of cultivation added with the Compounds (1), (2) and (3) were compared with the result of the control which was not added with any compound.

Experimental System

Cell used: KB Cell (Originating from Human Mouth Epidermal Cancer),
Culture medium: Eagles Minimal Essential Medium supplemented with 10% Calf Serum,
Cultivation: 37° C. Carbon dioxide Gas incubator (5% $CO_2$).

Method of Experiment

Day 0:
KB cells were diluted in the culture medium to adjust the KB cell density to 2 x $10^4$/ml.
Three ml of the cell suspension was inoculated in each of 60 mm plastic dishes.
Two dishes per standard dosage were used.
Day 1:
Test compound was added to the medium so that the final concentrations were set to 100, 30, 10, 3 and 1 μg/ml.
Day 4:
Cells were scraped off from the dish using trypsin, and the cell number was countered using a Corter counter.

Criteria for Judgment

In general accordance with the stipulations set forth by the National Cancer Institute (NCI), U.S.A., the concentration of compound necessary for exerting 50% growth inhibition ($ED_{50}$) compared to the control was determined. A compound was judged as effective when ED50 was less than 4 μg/ml.

The results are shown below.

TABLE I

Result of Test on Carcinostatic Effect
(Effect of Inhibiting growth of KB-Cell)

| Compound No. Tested | Concentration (μg/ml) | Inhibition Rate (%) |
| --- | --- | --- |
| 1 | 0.3 | 50 |
| 2 | 1.15 | 50 |
| 4 | 0.3 | 50 |
| Control | 0 | 0 |

TEST EXAMPLE 2

Effect on Prolongation of Life Span in Cancer implanted Mouse and Acute Toxicity Pharmacological effects of the compounds as used in Test Example 1 were tested in vivo using P-388 implanted mice. The results were compared to that of a control which did not contain any test compound.

System Used in Experiment

Animal Used: CDF Mouse (6 mice/group),
Tumor: P-388,
Number of Inowlated Cells: $10^6$ cells/mouse,
Inowlated Site; i.p.,
Day of Administration: Day 1 and Day 5,
Dosage: $LD_{50}$ or 400 mg/kg/day at the maximum.

Criteria for Judgment

The treatment was judged as effective when the ratio of survival of the treated group to that of the control group (T/C %) was 120% or more. The survival period of the control group was generally about 10 days.

TABLE II

Effect on Prolongation of Life Span of Mouse implanted with P-388 Cancer Cells

| Compound No. Tested | Dosage (mg/kg) | Ratio of Life Prolongation (%) |
| --- | --- | --- |
| 1 | 25 | 111 |
|   | 12.5 | 203 |
|   | 6.25 | 300 |
| 2 | 400 | 130 |
|   | 200 | 130 |
|   | 100 | 122 |
| 3 | 200 | 204 |
|   | 100 | 163 |
|   | 50 | 157 |

What is claimed is:

1. An indoloquinoline system compound represented by the following formula (1):

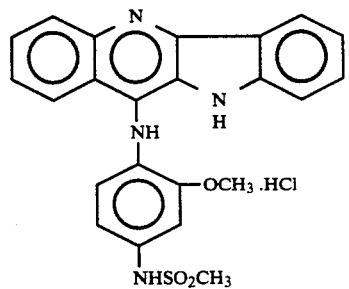

(1)

2. A pharmaceutical composition for carcinostatic treatment of epithelial tumors comprising a therapeutically effective amount of the indoloquinoline compound of claim 1 and a pharmaceutically acceptable carrier.

* * * * *